US007371518B2

(12) United States Patent
Lorincz et al.

(10) Patent No.: US 7,371,518 B2
(45) Date of Patent: May 13, 2008

(54) UNIVERSAL COLLECTION MEDIUM

(75) Inventors: Attila T. Lorincz, North Potomac, MD (US); Yanlin Tang, Rockville, MD (US)

(73) Assignee: Digene Corporation, Gaithersburg, MD (US)

( * ) Notice: Subject to any disclaimer, the term of this patent is extended or adjusted under 35 U.S.C. 154(b) by 244 days.

(21) Appl. No.: 10/351,149

(22) Filed: Jan. 24, 2003

(65) Prior Publication Data

US 2003/0119049 A1    Jun. 26, 2003

Related U.S. Application Data

(63) Continuation of application No. 09/598,571, filed on Jun. 21, 2000, now abandoned.

(51) Int. Cl.
*C12Q 1/28* (2006.01)
*G01N 1/28* (2006.01)

(52) U.S. Cl. .......................................... 435/6; 435/40.5

(58) Field of Classification Search ................ 435/6; 436/94
See application file for complete search history.

(56) References Cited

U.S. PATENT DOCUMENTS

| | | | |
|---|---|---|---|
| 4,465,078 A | | 8/1984 | Manning et al. |
| 4,578,282 A | | 3/1986 | Harrison |
| 4,888,278 A | | 12/1989 | Singer et al. |
| 5,256,571 A | | 10/1993 | Hurley et al. |
| 5,357,977 A | | 10/1994 | Michels |
| 5,370,128 A | | 12/1994 | Wainwright |
| 5,543,294 A | | 8/1996 | Silverstein et al. |
| 5,580,970 A | | 12/1996 | Hendricks et al. |
| 5,679,333 A | * | 10/1997 | Dunphy ........................ 424/75 |
| 5,976,829 A | * | 11/1999 | Birnboim .................... 435/40.5 |

FOREIGN PATENT DOCUMENTS

| EP | 0 502 994 B1 | 9/1992 |
|---|---|---|
| WO | WO 9108312 | 6/1991 |
| WO | 94/02645 | 3/1994 |

OTHER PUBLICATIONS

Tokuda et al. Fundamental study on the mechanism of DNA degradation i tissues fixed in formaldehyde. J. Clin. Pathol. vol. 43, pp. 748-751 (1990).*

Makkus et al. Practical Aspects of Fixatives in High Resolution Nuclear Image Analysis. Cytometry vol. 15, pp. 302-310 (1994).*

Milde et al. Improved DNA typing of human urine by adding EDTA. Int. J. Legal Med. vol. 112, pp. 209-210 (1999).*

H. zur Hauzen, Papillomavirus Infections-A Major Cause of Human Cancers, *Biochimica et Biophisica Acta*, 1228, Mar. 6, 1996, pp. F55-F78.

Lubomir P. Turek, et al., The Genetic Program of Genital Human Papillomaviruses in Infection and Cancer, *Obstetrics and Gynecology Clinics of North America*, vol. 23, No. 4, Dec. 1996, pp. 735-758.

Lubomir P.Turek, The Structure, Function, and Regulation of Papillomaviral Genes in Infection and Cervical Cancer, *Advances in Virus Research*, vol. 44, 1994, pp. 305-356.

E.M. Hsu, et al., Quantification of HPV-16 E6-E7 Transcription in Cervical Intraepithelial Neoplasia by Reverse Transcriptase Polymerase Chain Reaction, *Int. J. Cancer*, vol. 55, Apr. 2, 1993, pp. 397-401.

Mohammed Nasseri, et al., Human Papillomavirus Type 16 Immortalized Cervical Keratinocytes Contain Transcripts Encoding E6, E7, and E2 Initiated at The P97 Promoter and Express High Levels of E7, *Virology*, vol. 184. Feb. 15, 1991, pp. 131-140.

P. Fernandez, et al., "Reverse Transcription—Polymerase Chain Reaction-Based Methology to Quantify Differential Gene Expression Directly From Microdissected Regions of Frozen Tissue Sections", *Molecular Carcinogenesis*, (1997), vol. 20, pp. 317-326.

N. Charuruks, et al., "In situ Hybridization : A New Tool in Molecular Medicine", *Journal of the Medical Association of Thailand*, vol. 79, No. 6, Jun. 1996, pp. 374-380).

P. Komminoth, et al., "In-situ polymerase chain reaction", *Virchows Archiv, B Cell Pathology Including Molecular Pathology*, vol. 64, No. 2, 1993, pp. 67-73).

A. M. McNicol, et al., "In Situ Hybridization and Its Diagnostic Applications in Pathology", *Journal of Pathology*, vol. 182, 1997, pp. 250-261.

\* cited by examiner

*Primary Examiner*—John S Brusca
(74) *Attorney, Agent, or Firm*—Morgan & Finnegan, LLP

(57) ABSTRACT

This invention provides a novel universal collection medium for cell collection. The medium allows for the first time the ability to perform cytology and direct molecular analysis on cells preserved in a single sample. This invention also provides novel methods for analyzing cells to assess human conditions.

14 Claims, 11 Drawing Sheets

UNIVERSAL COLLECTION MEDIUM

This is a continuation of prior application Ser. No. 09/598,571, filed Jun. 21, 2000 now abandoned, to which priority under 35 U.S.C. §120 is claimed.

FIELD OF THE INVENTION

The present invention is generally related to the field of cytological and molecular assays and specifically to the area of assays for the assessment of conditions using cytological and molecular assays.

BACKGROUND OF THE INVENTION

The detection and diagnosis of human conditions is of obvious importance for the treatment of disease. Numerous characteristics of diseases have been identified and many are used for their diagnosis. Many diseases are preceded by, and are characterized by, changes in the state of the affected cells. Changes can include the expression of viral genes in infected cells, changes in the expression patterns of genes in affected cells, and changes in cell morphology. The detection, diagnosis, and monitoring of diseases can be aided by the assessment of such cell states.

Routinely, for patients suspected of having one or more infectious diseases, for example human papilloma virus or herpes simplex virus, a sample of cells is taken from the patient for analysis. Generally, such a sample is in the form of a swipe or cellular scrape from the area primarily affected by the disease. These swipes usually collect a mixture of normal and diseased cells with a very limited total number of cells. The collected cells are traditionally smeared onto a slide for further analysis. When biochemical analysis was attempted, it was done at the expense of a cytological analysis and was done via qualitative methods such as in situ hybridization.

Routinely, the cervical sample obtained for conventional cytology is smeared onto a slide for morphological analysis. If this sample identifies potential disease by cell cytology, the patient must return for colposcopy to have a second sample collected for repeat cytology and/or genetic analysis and other molecular tests such DNA, RNA or protein. Recently, liquid cytology media have appeared on the market, which provide for enhanced morphology. These media were discovered to be amendable to molecular tests such as for HPV DNA, however, cells are routinely collected into 10-20 ml of preserving agents, which excessively dilute DNA, RNA and other asssayable biomolecules, making molecular testing less than ideal. Further, while the current preserving reagents preserve cellular morphology these reagents allow degradation of DNA and RNA, such that quantitative analysis becomes difficult or impossible upon storage.

Thus, present day analysis requires at least two samples to be obtained from a patient in order to determine cell morphology and quantitative genetic analysis. Current cytology methods use large volumes of a preserving agent which excessively dilute DNA, RNA and other assayable biomolecules. Further, while the current preserving reagents preserve cellular morphology these reagents allow degradation of individual biomolecules such as DNA, RNA and protein, such that quantitative analysis becomes impossible.

Designing methods and media to preserve cells or tissue for analysis by both morphological and biochemical analysis has proven problematic in the past. For example, fixing cells or tissue for morphological analysis compromised the ability to do biochemical analysis. Preserving cellular RNA was done at the expense of DNA and morphological analysis. Similarly, preserving cellular DNA was done at the expense of RNA and morphological analysis.

It is an object of the present invention to provide a general collection medium for identifying cellular morphology and quantitatively preserving DNA, RNA and other biomolecules from a single sample regardless of the disease to be detected.

It is another object of the present invention to provide a universal cell collection medium for preserving cell morphology and nucleic acids, lipids, carbohydrates, or proteins in a cell sample where limited numbers of cells are available in the sample.

It is another object of the present invention to provide compositions and methods for solution-based direct analysis of biomolecules of interest. The methods and compositions of this invention solve problems encountered in non-solution-based methods such as in situ hybridization or non-direct methods which require separation of the biomolecule of interest from other cellular components before analysis.

SUMMARY OF THE INVENTION

The present invention relates to the detection, analysis and monitoring of cellular disease. A new cell collection medium is disclosed which preserves both cell morphology and cellular biomolecules for quantitative analysis in a cell sample so that multiple assays can be carried out from a single patient sample. The state of the cells can be assessed using a device for collecting cellular samples in a small volume.

One embodiment of the present invention involves examining the cell morphology and detecting a specific DNA sequence or measuring the levels of expression of genes involved in a cell state, and comparing their expression to each other or to reference genes in a specific ratio, as an indication of the state of a disease in the cells. This method can be used to detect and/or monitor the onset or progression of any human condition which causes a change in cell morphology or in levels or structures of specific biomolecules. For example, the present invention can be used to assess predisposition to a particular disease or to assess the stage or risk of a disease as indicated by the state of the cells. It can also be used to guide or assess the effectiveness of a therapy for a disease by identifying appropriate therapy based on the indicated cell state or by indicating any change in the state of cells subjected to the therapy.

In an other embodiment of the invention, a universal cell collection medium is disclosed. This medium allows simultaneous preservation of cell morphology and biomolecules in a small volume. Also embodied in the present invention is a device for collecting such cell samples.

In a further embodiment of the invention, methods and compositions are provided wherein a sample is analyzed according to cell morphology and biochemical analysis in solution phase. The biochemical analysis is either qualitative or quantitative and directly analyzes RNA, DNA, protein, carbohydrate or any combination thereof.

BRIEF DESCRIPTION OF THE DRAWINGS

FIG. 9. UCM 130, 6 weeks at RT. CaSki cells. Magnification×400. H&E staining.

FIG. 10. PreservCyt (134), baseline (12 hours at RT). CaSki cells. Magnification×200. H&E staining.

FIG. 11. PreservCyt (134), 3 weeks at RT. CaSki cells. Magnification×200. H&E staining.

FIG. 12. PreservCyt (134), 6 weeks at RT. CaSki cells. Magnification×400. H&E staining.

DETAILED DESCRIPTION OF THE INVENTION

Figures 1, 2, 3, 4:
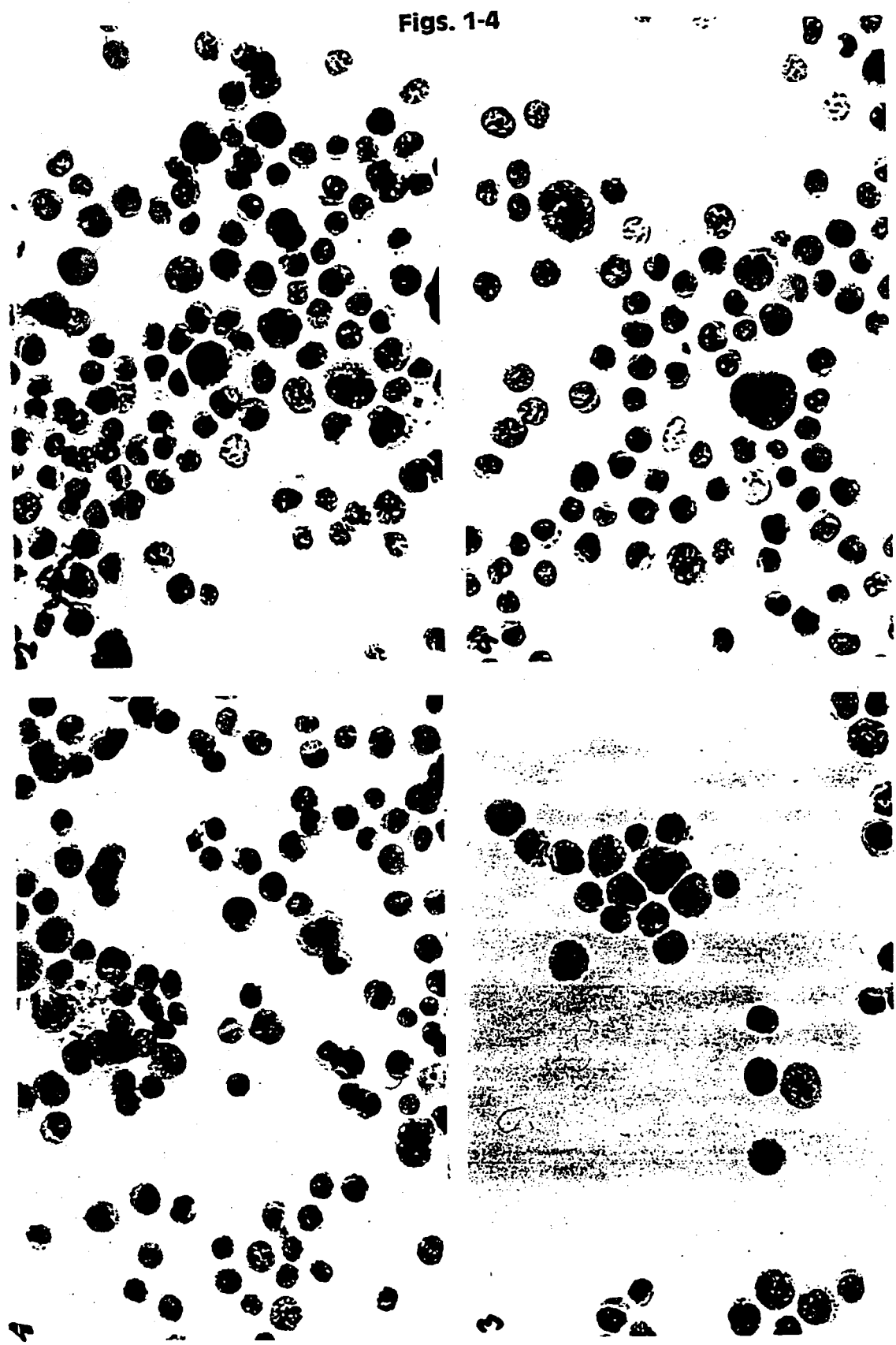
FIG. 1. UCM 127, baseline (12 hours at RT). CaSki cells. Magnification×200. Papanicolaou staining.
FIG. 2. UCM 127, 3 weeks at RT. CaSki cells. Magnification×200. Papanicolaou staining.
FIG. 3. UCM 127, 6 weeks at RT. CaSki cells. Magnification×200. H&E staining.
FIG. 4. UCM 128, (12 hours at RT). CaSki cells. Magnification×200. Papanicolaou staining.
Figures 5, 6, 7, 8:
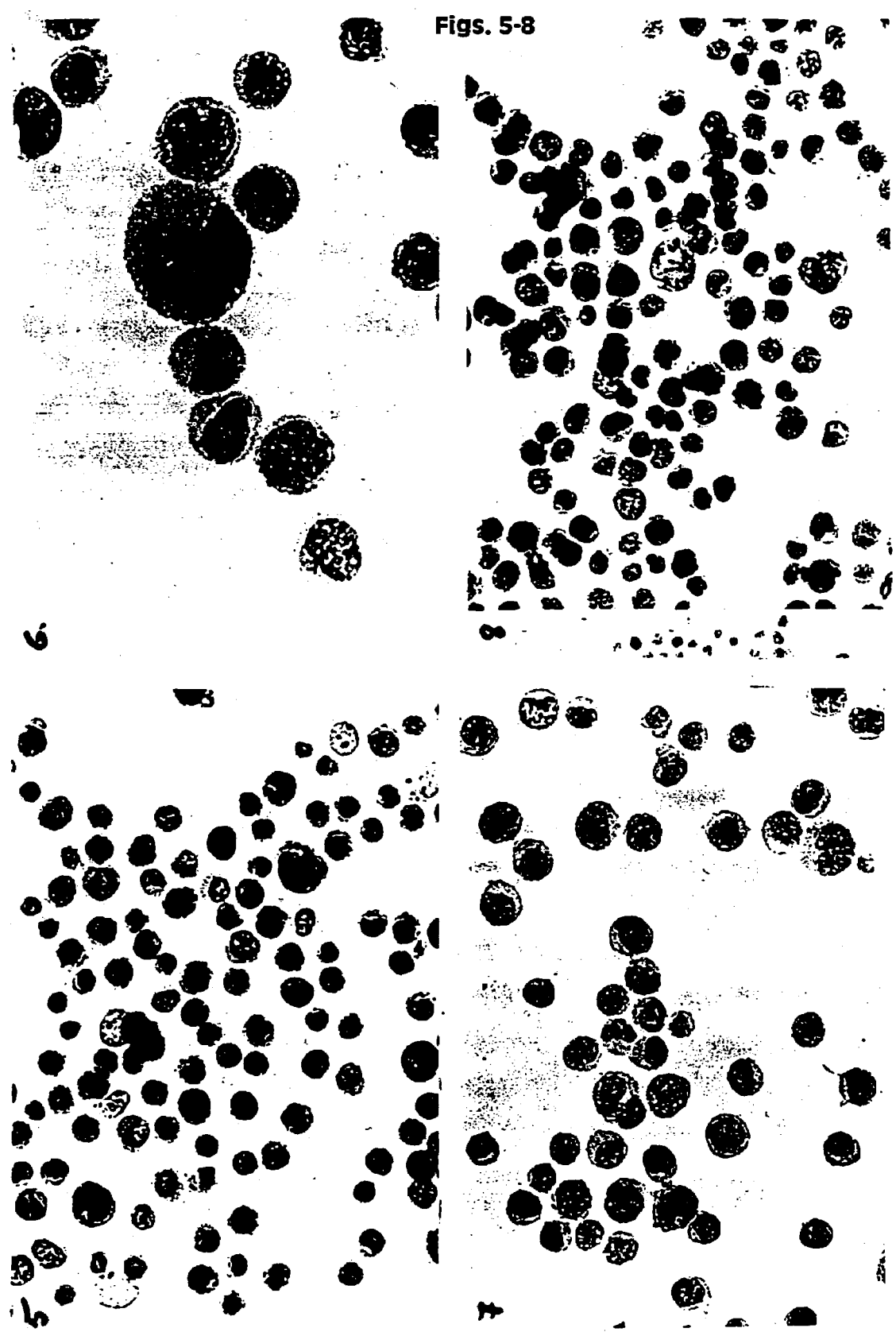
FIG. 5. UCM 128, 3 weeks at RT. CaSki cells. Magnification×200. Papanicolaou staining.
FIG. 6. UCM 128, 6 weeks at RT. CaSki cells. Magnification×400. H&E staining
FIG. 7. UCM 130, baseline (12 hours at RT). CaSki cells. Magnification×200. H&E staining.
FIG. 8. UCM 130, 3 weeks at RT. CaSki cells. Magnification×200. Papanicolaou staining.
Figures 13, 14, 15, 16:
FIG. 13. CytoRich (135), baseline (12 hours at RT). CaSki cells. Magnification×200. Papanicolaou staining.
FIG. 14. CytoRich (135), 3 weeks at RT. CaSki cells. Magnification×200. Papanicolaou staining.
FIG. 15. CytoRich (135), 6 weeks at RT. CaSki cells. Magnification×400. H&E staining.
FIG. 16. UCM 141, 6 weeks at RT. CaSki cells. Magnification×400. H&E staining.
Figures 17, 18, 19, 20:
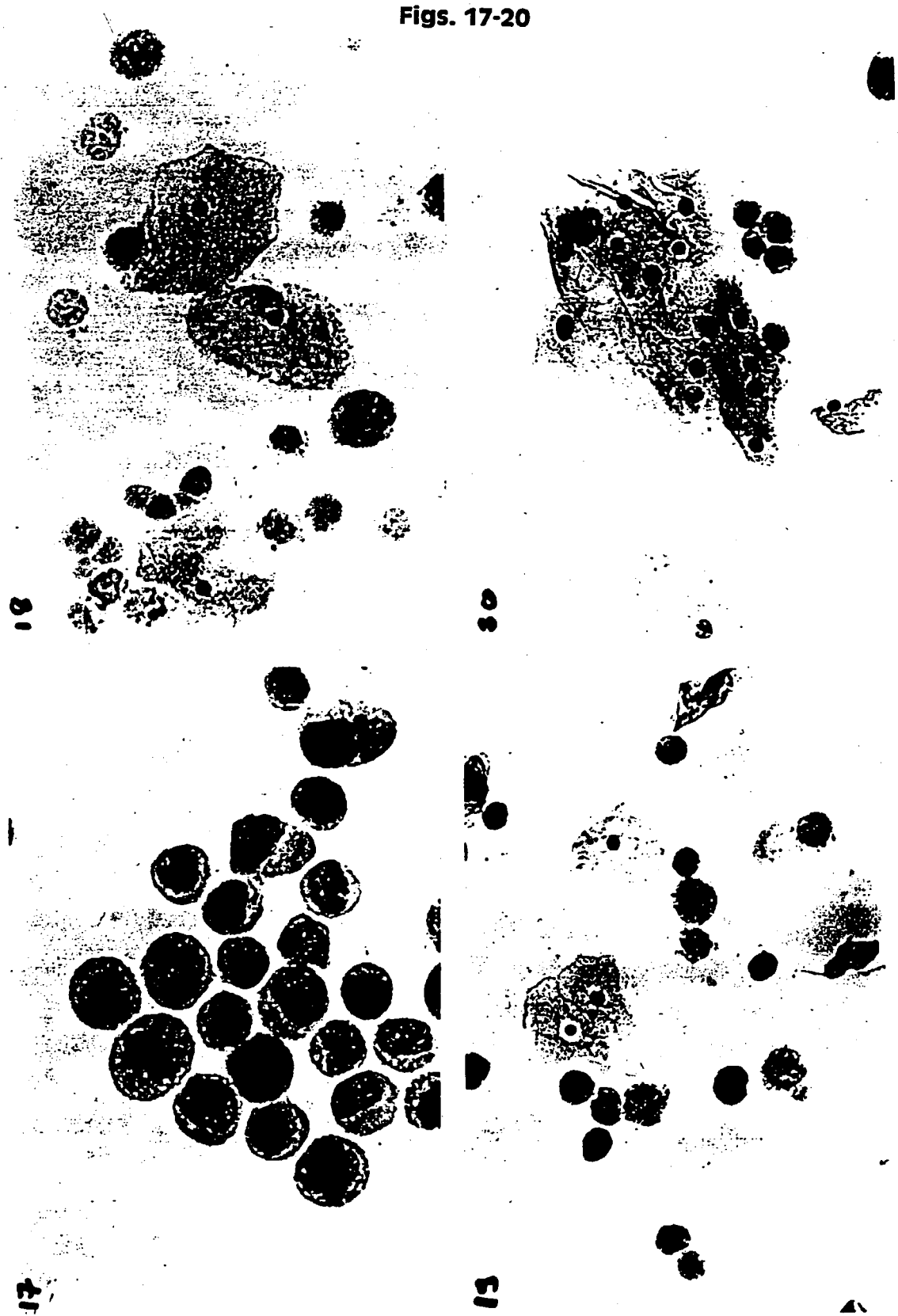
FIG. 17. UCM 149, 6 weeks at RT. CaSki cells. Magnification×400. H&E staining.
FIG. 18. UCM 141, baseline at RT. Normal epithelial and CaSki cells. Magnification×200.
FIG. 19. UCM 141, baseline at 4° C. Normal epithelial and CaSki cells. Magnification×200.
FIG. 20. UCM 141, 10 days at RT. Normal epithelial and CaSki cells. Magnification×200.
Figures 21, 22, 23, 24:
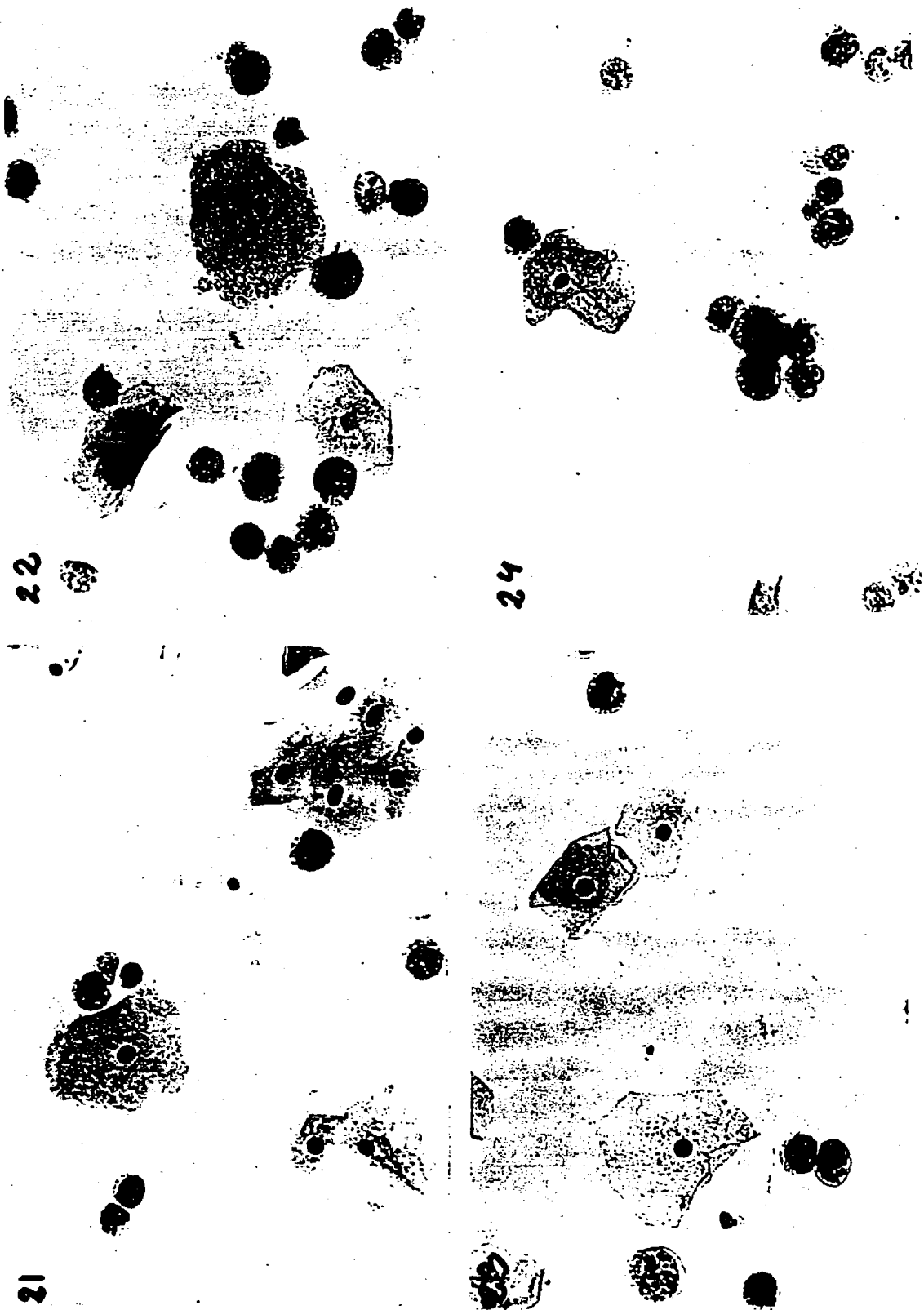
FIG. 21. UCM 141, 10 days at 4° C. Normal epithelial and CaSki cells. Magnification×200.
FIG. 22. UCM 141, 10 days at RT. Normal epithelial and CaSki cells. Magnification×200.
FIG. 23. UCM 141, 10 days at 4° C. Normal epithelial and CaSki cells. Magnification×200.
FIG. 24. UCM 149, baseline at RT. Normal epithelial and CaSki cells. Magnification×200.
Figures 25, 26, 27, 28:
FIG. 25. UCM 149, baseline at 4° C. Normal epithelial and CaSki cells. Magnification×200.
FIG. 26. UCM 149, 10 days at RT. Normal epithelial and CaSki cells. Magnification×200.
FIG. 27. UCM 149, 10 days at 4° C. Normal epithelial and CaSki cells. Magnification×200.
FIG. 28. UCM 149, 3 weeks at RT. Normal epithelial and CaSki cells. Magnification×200.
Figures 29, 30, 31, 32:
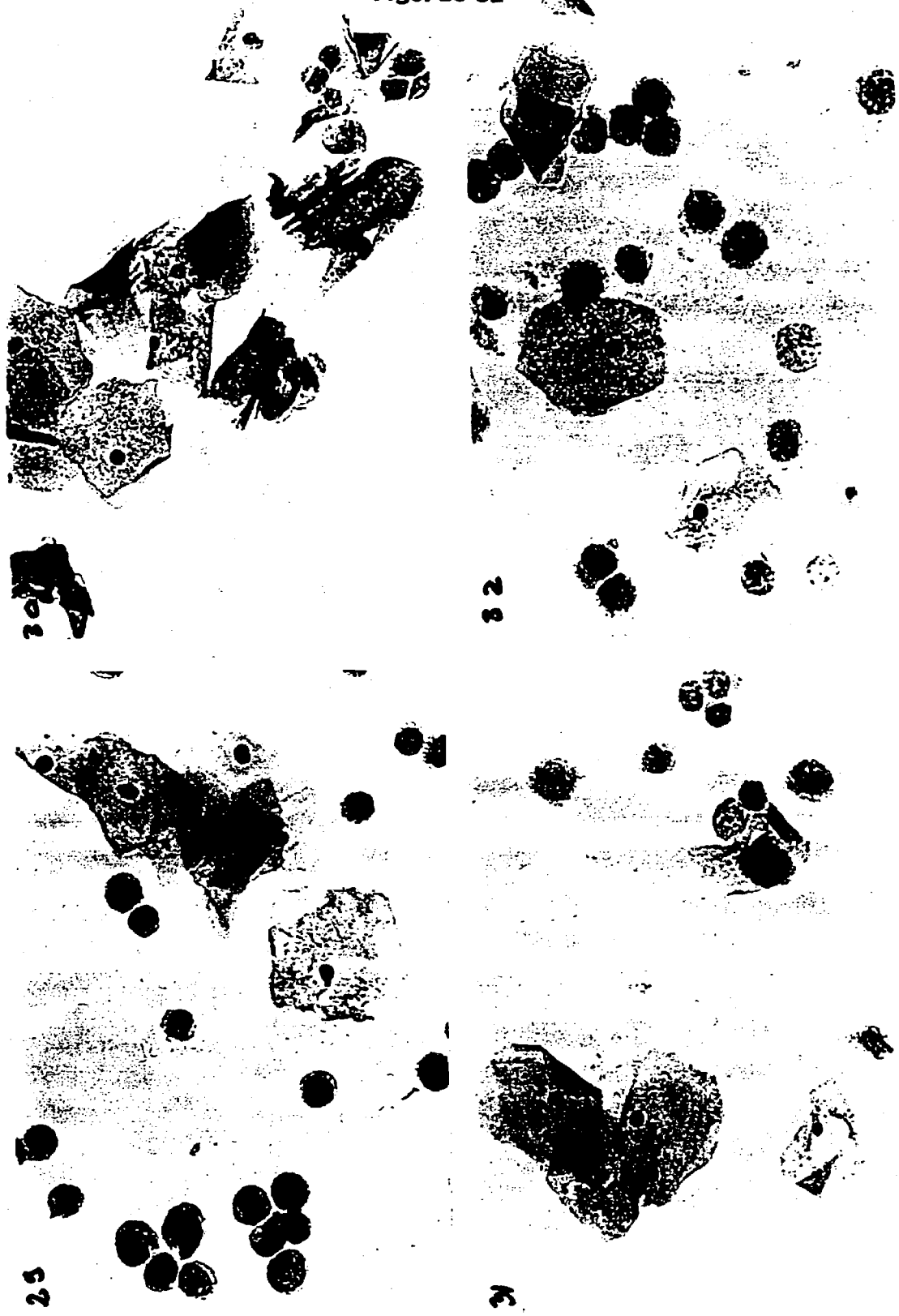
FIG. 29. UCM 149, 3 weeks at 4° C. Normal epithelial and CaSki cells. Magnification×200.
FIG. 30. PreservCyt, baseline at RT. Normal epithelial and CaSki cells. Magnification×200.
FIG. 31. PreservCyt, baseline at 4° C. Normal epithelial and CaSki cells. Magnification×200.
FIG. 32. PreservCyt, 10 days at RT. Normal epithelial and CaSki cells. Magnification×200.
Figures 33, 34, 35, 36:
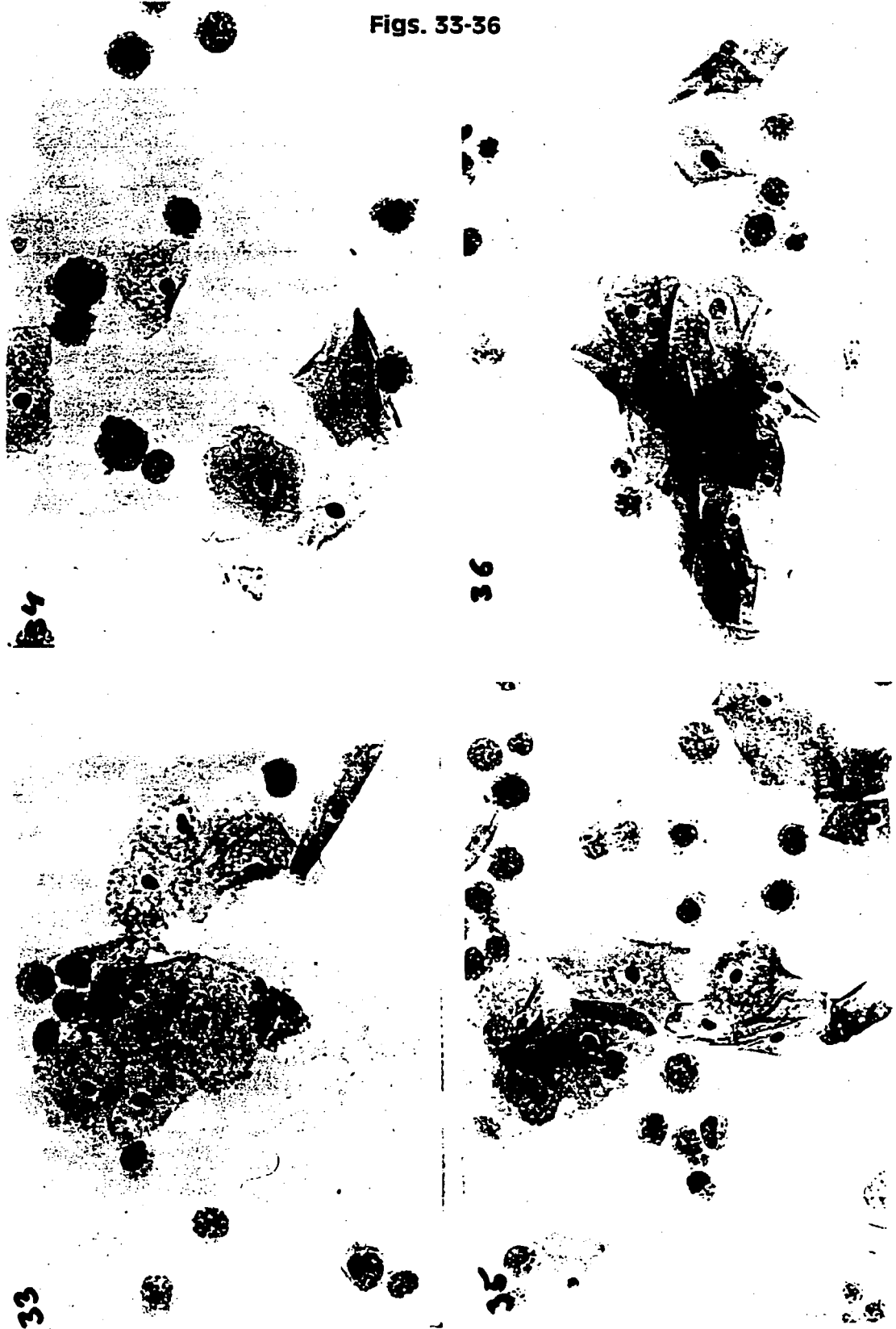
FIG. 33. PreservCyt, 10 days at 4° C. Normal epithelial and CaSki cells. Magnification×200.
FIG. 34. PreservCyt, 3 weeks at RT. Normal epithelial and CaSki cells. Magnification×200.
FIG. 35. PreservCyt, 3 weeks at 4° C. Normal epithelial and CaSki cells. Magnification×200.
FIG. 36. CytoRich, baseline at RT. Normal epithelial and CaSki cells. Magnification×200.
Figures 37, 38, 39, 40:
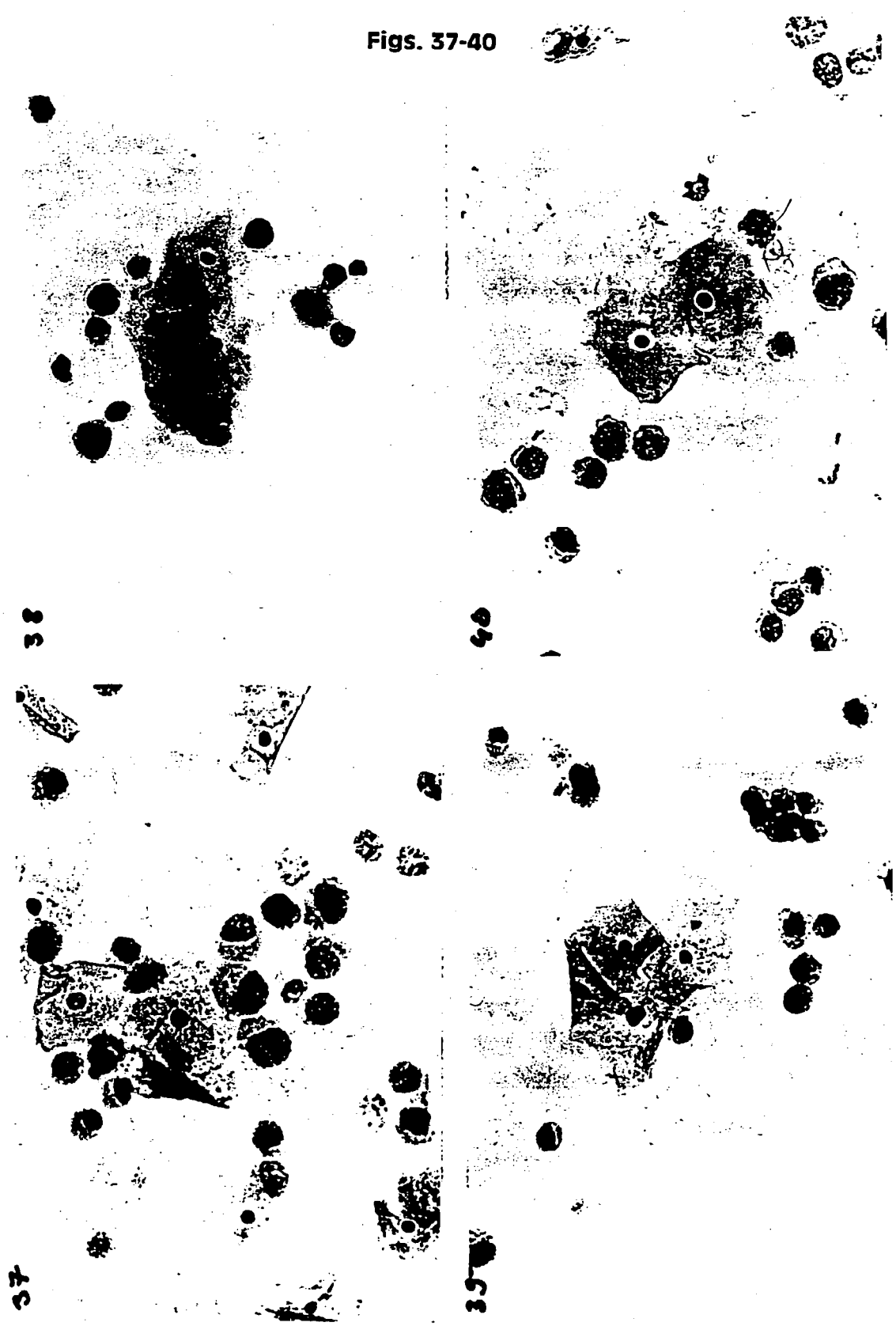
FIG. 37. CytoRich, baseline at 4° C. Normal epithelial and CaSki cells. Magnification×200.
FIG. 38. CytoRich, 10 days at RT. Normal epithelial and CaSki cells. Magnification×200.
FIG. 39. CytoRich, 10 days at 4° C. Normal epithelial and CaSki cells. Magnification×200.
FIG. 40. CytoRich, 3 weeks at RT. Normal epithelial and CaSki cells. Magnification×200.
Figure 41:
FIG. 41. CytoRich, 3 weeks at 4° C. Normal epithelial and CaSki cells. Magnification×200.

The present invention relates to a universal cell collection medium that makes it possible to conveniently collect and preserve cells and their contents for assessment of the existence or progression of a disease isolated from a single small patient sample, using cytological assays, molecular assays, or both.

The instant universal cell collection medium preserves cell morphology and preserves macromolecules in a cell sample for either qualitative or quantitative analysis. One useful form of the disclosed cell collection medium preserves nucleic acids in the cells. Such preservation can be limited to refrigerated samples. Alternatively, preserved samples can be kept at ambient temperatures. Different forms of the universal collection medium preserve a sample for days or weeks or more. The universal cell collection medium can be used to collect cell samples for any purpose and is not limited to use with any particular assay method. Some forms of the universal collection medium contain a buffered saline isotonic solution or an alcoholic solution such as methanol, ethanol, or a similar alcohol, an RNase inhibitor such as RNasin, and a protease inhibitor such as pepstatin. Many different nuclease inhibitors are known in the art, including, for example, vanadate complexes, chelating agents and detergent-based compounds as well as specific inhibitors such as RNasin. Any known nuclease and/or protease inhibitors can be employed in the present invention as a component of the universal collection medium in order to preserve the particular molecules of interest in the a sample.

The formulations of this invention provide for the first time means for performing cytological and molecular analysis on cells which are contained in a single sample. The cells are obtained from a patient and stored in the UCM of this invention. From this single sample, cells are extracted and a cytological examination is performed, the cellular DNA is qualitatively or quantitatively examined, the cellular RNA is qualitatively or quantitatively examined, or any combination of analysis is performed. The different analyses are performed concurrently or, for example, after the results of the cytological analysis are obtained, the cells are subjected to molecular analysis days, weeks or even months later. Conversely, after molecular analysis of the cells contained in the UCM, for example by automated screening, the sample is retrieved for cytological analysis, days, weeks or even months later.

In one embodiment of the invention the universal collection medium (UCM) formulations of this invention are buffered, water-based solutions which comprise a preservative such as a mixture of one or more alcohols, a cross-linking agent and an agent to inhibit degradation of RNA, DNA and protein. The use of the UCM formulation is further enhanced by the addition of an antimicrobial agent.

Nearly any non-viscous alcohol can be used to formulate the UCM, for example, any C1 to C10 alcohols or mixtures thereof can be used. Preferred alcohols include methanol, ethanol, propanols, butanols, and pentanols. Most preferred are ethanol and n-butanol. The alcohol can comprise a significant percentage of the formulation. For example, the alcohol(s) component can comprise about 1% to about 75% of the UCM formulation. More preferred is the percentage range of about 1% to about 50% alcohol and more preferred is about 5% to about 30% alcohol in the UCM formulation. A range of about 5% to about 15% alcohol is also preferred.

The pH range of the UCM formulation is important for maintaining the cellular biochemical and morphological integrity of the cells. A pH range of about 2.5 to about 6 is used to formulate the UCM of this invention. More preferred is a pH range of about 3 to about 5 and most preferred is a pH range of about 3.5 to about 4.5. Buffer(s) are used to maintain the pH of the UCM at a constant value. Any buffer that has buffering capacity in the indicated pH range can be used in the UCM of this invention. Non-limiting examples of buffer components include glycine, maleic, phosphoric, tartaric, citric, formic, or acetic acids and the like.

The cross-linking agents of this invention comprise about 1% to about 25% of the UCM formulation. Preferably, the cross-linking agents comprise about 1% to about 15% or from about 1% to about 10%. Most preferably, the cross-linking agent comprises about 1% to about 5% of the UCM formulation. Cross-linking agents (also known as fixatives) are well-known in the art (see, for example, Stedman's Medical Dictionary, 25th Edition, Williams & Wilkins, Baltimore Md. 1990 at page 592) and their use in the UCM formulation is now readily apparent to those of skill in the art in light of the present invention. Non-limiting examples of the cross-linking agents for use in the UCM formulation include aldehydes such formaldehyde, glutaraldehyde and the like. A preferred cross-linking agent is glutaraldehyde-bisulfite.

Fixatives are defined by Stedman's as "serving to fix, bind, or make firm or stable." They are substances "used for the preservation of gross and histologic specimens of tissue, or individual cells, usually by denaturing and precipitation or cross-linking the protein constituents." Non-limiting examples of such fixatives for use according to the present invention are polymers such as poly(ethylene glycols) and poly(ethylene oxides). Poly(ethylene glycols) are preferred and poly(ethylene glycols) ("PEG") with a molecular weight of between about 600 and about 4,600 are more preferred. PEG having a molecular weight of 1500 ("PEG-1500") is most preferred. Fixatives, which function in an equivalent manner to cross-linking agents for the purpose of this invention, are formulated as described above for cross-linking agents.

Agents able to inhibit degradation of RNA, DNA and/or protein are well-known in the art. They can work by either inhibiting enzymes or sequestering metal ions or both. Nuclease or protease inhibitors such as RNasin or pepstatin or chelating agents can be used according to this invention. Preferred agents to inhibit degradation of RNA, DNA and/or protein are chelating agents. Chelating agents are well-known in the art (see, for example, *Data For Biochemical Research*, Third Ed., Rex M. C. Dawson et al., Oxford University Press 1986, at chapter 17) and are known to both attenuate metal ion-induced and enzymatic degradation of biopolymers. Non-limiting examples of chelating agents for use in this invention include murexide, chromotropic acid, 1-(1-hydroxy-2-napththylazo)-2-hydroxy-5-nitronaphthalene-4-sulphonic acid, EDTA (ethylenediaminetetraacetic acid), o-phenanthroline, thiourea and the like. A preferred chelating agent is EDTA.

Antimicrobial agents for use in this invention are those known in the art. Non-limiting examples of antimicrobial agents are aminoglycosides, β-lactams, cephalosporins, macrolides, penicillins, azides and the like. A preferred antimicrobial agent is sodium azide.

The universal collection medium can be used for a combination of two or more assays of different characteristics related to a cell state of interest. As used herein, the assay or assays refer to detection or measurement of specific characteristics, the results of which may be combined with other such measurements of other characteristics to provide an overall assessment of a cell suspected of being infected with one or more diseases. These assays may include, for example, a combination of morphological analysis and quanitation of a particular RNA or DNA or protein or carbohydrate structure whose presence or levels provide a specific indication of the presence or progression of a disease.

The universal collection medium can be used to collect any desired cell sample. Cell samples are collected in any suitable manner, including scrapings, biopsy, or washings, and from any suitable source. Numerous cell collection techniques are known and any can be used with the present invention. Generally, the source of cells for a cell sample is chosen based on the known or likely tissue affected by the cell state of interest.

Cell samples for use in the present invention can be collected and stored in liquid medium. Examples of useful cell collection media are PreservCyt® (Cytyc), and CytoRich™ (Autocyte). These media were developed for the collection of cytological samples but can be adapted for use with molecular assays when modified as described herein.

Nucleic acid detection generally benefits from the use of a reagent capable of preventing nucleic acid degradation prior to performing the assay if the assay is not performed soon after sample collection. A useful medium is a preservative based collection medium that has stabilizers for nucleic acids (both RNA and DNA) and proteins and that preserves cell morphology, such as the universal collection medium of the present invention.

One method useful with the present invention involves measuring the levels of expression of genes involved in a disease state, and comparing their expression to each other or to reference genes, as an indication of the state of the cells. Such measurements can be combined with other assays to increase the accuracy and reliability of the assessment of the disease state. The present invention can be used to assess the stage of a disease as indicated by the state of the cells. This embodiment can also be used to guide or assess the effectiveness of a therapy for a disease by identifying appropriate therapy based on the indicated disease state or by indicating any change in the state of cells subjected to the therapy. Also disclosed is a cell collection medium for preserving cell morphology and cellular biomolecules in a cell sample so that multiple assays can be carried out on the same sample.

Many diseases and other human conditions are characterized by specific cellular phenotypes and gene expression patterns. Such diseases and conditions can be identified and/or monitored by assessment of specific cellular morphology or levels or structures of particular biomolecules. For example, neoplastic and cancerous cells generally exhibit certain distinctive morphologies and growth characteristics. Molecular characteristics, such as gene mutations and gene expression patterns are also a good indicator of disease progression. Virally infected cells can exhibit different morphologies and gene expression patterns, including expression of viral genes. Using the present invention, the characteristics of the cell state, such as changes in cell morphology and/or expression of genes can be determined from a patient sample.

The characteristics to be detected are specific to the cell state of interest and the disease suspected of being present in the cell sample. Such characteristics can be generally divided into two types, cytological characteristics and molecular characteristics. As used herein, cytological characteristics are characteristics such as, for example, overall cell shape and appearance of the cell and its organelles. The primary identification and classification of many neoplastic and cancerous cells has traditionally been accomplished using cytological characteristics. Identification of cytological characteristics is generally slow, requires a relatively high level of training, and generally cannot be easily automated. As used herein, molecular characteristics are the presence and/or absence and state of particular molecular species, such as proteins, nucleic acids, carbohydrates and metabolites. Such molecular characteristics are generally identified by detecting and/or quantifying the particular molecules of interest.

The present invention allows both cytological and molecular characteristics to be analyzed from a small patient sample. The characteristics assayed can include additional or surrogate marker characteristics that are not a direct cause or result of the disease but that are related to certain disease and cell states. Examples of such additional markers include polymorphic markers, human leukocyte antigens (HLA) such as B7 that predispose women for cervical carcinomas, oncogenes, p53 mutations, BRCA1/2 mutations, other cancer markers, oncosuppressors, cytokines, growth factor receptors, and hormones. Such markers can be present in, or absent from, cells exhibiting state- or disease-specific characteristics, and such presence or absence can be indicative of, for example, a more severe or less severe disease state. These markers can be used in conjunction with disclosed methods to infer either higher or lower risk of neoplastic disease depending on the number of abnormal scores or the magnitude of change in quantitative markers.

Examples of disease states for assessment using the present invention include, but are not limited to, autoimmune disorders, neoplasias, and cancer. Other disease states of interest include HPV-based disease including HPV infection, cervical intraepithelial neoplasia (CIN), and cancer, atypical squamous cells of undetermined significance (AS-CUS), warts, epidermo dysplasia verruciformis and other skin diseases, laryngeal papilloma, oral papilloma, conjunctival papilloma and prostate disease including enlarged prostate and prostate cancer, chlamydia, and viral infections such as HIV and herpes.

A cell sample as the term is used herein is primarily a collection of cells from a patient. One method of obtaining cells is through non-invasive means, which is defined herein as obtained without the puncturing of a patient. Examples of non-invasive means are, for example, cell samples obtained from urine or a nasal, epithelial, cervical or other cell surface scrape. Other methods for obtaining a cell sample are by needle biopsy, or tissue biopsy. The cells are collected into volumes of less than 10 ml. More preferably, the cells are collected into volumes of less than about 5 ml, and most preferred the cells are collected into volumes of less than about 2 ml.

Combinations of multiple assays may be used with the media and device of the present invention and can be carried out from the collection and use of a single sample. An important aspect of the combination of assays is the use of a universal cell collection medium that allows a single cell sample to be used for multiple assays of different types with a minimum number of assay-specific processing steps required. For example, cells for assaying cytological characteristics are typically collected in a large volume of liquid which leaves the cell sample too dilute for most assays of molecular characteristics. Prior art methods do not provide for direct methods for both cytological and molecular analysis. The prior art methods require several extra steps, such as a separate concentration step, which is inconvenient and may result in many of the molecular components of the cell being degraded. Cytological cell samples, while optimized for preserving cell morphology, generally do not preserve nucleic acids well; thus making the sample unusable for many molecular assays.

Cell samples for use in the method of the present invention can be fixed or processed in any manner consistent with the assays to be performed. For example, both cytological and molecular assays can be performed using cells fixed on a solid substrate such as a slide. Preferably, however, molecular assays are done in solution. The requirements of the assays to be performed will generally determine the sample processing to be used.

The types of comparisons described above can also be used with many different genes and disease states. That is, the measured level of expression of a gene of interest can be compared, for example, to the level of expression of the same type of gene in a different cell sample (such as an earlier cell sample from the same source or appropriate reference cells), to the level of expression of a different type of gene in the same or a different cell sample, to the level of expression of a reference gene in the same cell sample, or to the level of expression of a reference gene in reference cells.

Expression of genes of interest can be assessed using any suitable method. For example, RNA can be detected using hybridization, amplification, or sequencing techniques, and protein, like carbohydrate, can be detected using specific antibodies. Many techniques for the specific detection of gene expression, by detection of expression products, are known and can be used with the disclosed UCM. One technique for detecting and measuring the level of expression of genes of interest is detection of RNA transcribed from the genes of interest. For the most reliable comparisons, expression levels that are to be compared should be measured using the same technique and be performed in the same manner.

Useful techniques for measuring the level of expression of a gene of interest in a cell sample include the hybrid capture technique described in WO 93/10263 by Digene, PCR in situ hybridization techniques described by (Nuovo, 1997)), branched DNA assays (Chernoff (1997)), transcription mediated amplification (TMA); Stoflet (1988)), and polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, (1991); Landegren, (1993)). Numerous assays for the detection and measurement of gene expression products are known and can be adapted for the determination of the level of expression of genes of interest using the UCM-collected samples.

The present invention provides methods for analyzing cells that previously were unavailable. For example, a combination of cancerous and non-cancerous cells were placed in a Universal Collection Medium according to this invention. The morphology of the cells was examined after storage at either 4° C. or room temperature for periods of 12 hours, 10 days, 3 weeks and 6 weeks. Slides were prepared by staining using procedures well-known in the art, for example, Papanicolaou staining and Hematoxylin and Eosin (H&E). When the slides were examined under a light microscope, all the features characteristic for cancer cells were visible and well-preserved in all cases. The slides showed large and hyperchromatic nuclei, usually with oval shape and irregular, granular chromatin, scanty cytoplasm, multinucleated cells, presence of nucleoli and presence of mitotic figures. In addition, the slides showed that there was good cell dispersion and no cell clumping. Both types of cells (normal and cancerous) had distinct and sharp shapes of both the nuclei and cytoplasm. The nuclei were well-stained and the normal cells showed a different color of cytoplasm depending on the maturity of the cell.

In one embodiment of the present invention RNA was analyzed directly by solution based procedures. The cells were first lysed by adding a proteolytic enzyme to the cells contained in wells of a microtiter plate. Non-limiting examples of enzymes for use in the present invention include proteinase K or Pronase. Cells can also be subjected to detergent lysis or osmotic lysis or a French Press. After incubation, biotinylated DNA probes were added to each well. The RNA:DNA hybrids were captured onto a solid phase by transferring to streptavidin coated microplates. Alkaline phosphatase-conjugated antibodies to RNA:DNA hybrids were added to each well in the hybridization microplate and signals were generated by adding a chemiluminescent reagent such as CDP-Star™ with Emerald II (Tropix) to each well. The signal was read from the microplate. The solution based DNA analysis was performed similarly to the RNA analysis except that the microtiter plates were coated with anti-RNA:DNA hybrid antibodies and the probes were unlabeled RNA probes.

The present invention can be conveniently performed using kits that include one or more of the materials needed for the method, such as reagents and sample collection and handling materials. For example, kits can include cell collection medium including sample preserving reagents, reagents for specific detection of DNA sequences, RNA sequences and/or expression products (mRNA or protein) of one or more DNA sequences, and sample handling containers. Useful reagents for detection of DNA sequences and/or RNA sequences are nucleic acid probes or protein nucleic acid probes for those sequences. Useful reagents for detection of DNA sequence expression products (proteins) are antibodies. Aberrant carbohydrate antigens associated with cancerous cells can also be detected by antibodies. A kit may also contain control samples or reagents, or reagents and materials for performing other assays to be combined with the disclosed assay.

The present invention can be performed using devices adapted to the method. Numerous devices for performing similar assays are known and in use and can be adapted for use with the disclosed UCM formulations, assays and methods. For example, devices are known for automating all or a part of sample assays and sample handling in assays.

All or part of the disclosed method can be controlled or managed using special purpose computer programs. The data collected from the disclosed method, and data from any other assay used in combination, can be compiled, analyzed, and output in various forms and for various purposes using special purpose computer programs. Such programs can be used with, or combined into, other patient or data management computer programs. The usefulness of such a program increases with the number of measurements or assessments to be combined, and the relative importance of each type of measurement to the overall assessment. Computer programs for use with the disclosed method can be used on general purpose computers, or can be incorporated into special purpose computers or computerized devices for controlling the disclosed method, handling and analyzing data from the disclosed method, or both.

EXAMPLES

The examples herein are meant to exemplify the various aspects of carrying out the invention and are not intended to limit the invention in any way.

Formulations

Formulation 127
  20% Ethanol
  0.05% NaN$_3$
  5 mM EDTA
  2.5% Glutaraldehyde-Sodium-Bisulfite (G-S-B)
  0.2 M NaOAc-HOAc
  pH 3.7

Formulation 128
  20% Ethanol
  0.05% NaN$_3$
  5 mM EDTA
  2.5% Glutaraldehyde-Sodium-Bisulfite (G-S-B)
  0.2 M NaOAc-HOAc
  pH 4.1

Formulation 130
  7% Butanol
  0.05% NaN$_3$
  5 mM EDTA
  2.5% Glutaraldehyde-Sodium-Bisulfite (G-S-B)
  0.2 M NaOAc-HOAc
  pH 3.7

Formulation 134
  PreservCyt® (Cytyc Corporation)
  Contains buffered methanol
  Storage limits with cytologic samples: 3 weeks at 4° C.-37° C.

Formulation 135
  CytoRich™ (AutoCyte Corporation)
  Contains less than 24% alcohol
  Storage 15° C.-30° C.

Formulation 141
  20% Ethanol
  0.05% NaN$_3$
  5 mM EDTA
  2.5% Glutaraldehyde-Sodium-Bisulfite (G-S-B)
  0.2 M NaOAc-HOAc
  pH 4.4

Formulation 149
  10% Butanol
  0.05% NaN$_3$
  5 mM EDTA
  2.5% Glutaraldehyde-Sodium-Bisulfite (G-S-B)
  0.2 M NaOAc-HOAc
  pH 4.4

Formulation 167
  9% Butanol
  0.05% NaN$_3$
  5 mM EDTA
  2% PEG-1500
  10 mM NaOAc-HOAc
  pH 4.5

Example 1

General Methods for Nucleic Acid Analysis

The assay for nucleic acids follows in general principle the method for detecting HIV RNA by the Digene Hybrid Capture HIV Test, described in WO 93/10263 by Digene. Briefly, following lysis, 50 µl of probe mix (containing DNA biotinylated probe) was added to each well. The plate was sealed and incubated at 65° C. for 1.5 hours for hybridization to occur. After hybridization, samples were transferred to a strepavidin-coated microplate, and 25 µL of anti-hybrid antibody was added to each well. The plate was agitated at 1100 RPM, for 1 hour, at room temperature. Wells were washed 6X times with 65° C. wash buffer, followed by one wash using distilled water. 100 µl of a chemiluminescent substrate was added to each well and the plate was incubated at room temperature for 30 minutes. The plate was then read in the DML 2000 luminometer. The data was then expressed as signal-to-noise. Using a calibration curve, the chemiluminescent signal generated by each specimen was converted into mRNA copies per cell.

Example 2

General Methods for Morphological Analysis

HPV 16 positive cancer cells (CaSki) were placed in UCM 127, 128, 141, 130, 149 and in two commercially available fixatives PreservCyt (Cytyc Corp.) and CytoRich (AutoCyte). The samples were then stored at ambient temperature. The baseline slides were prepared after 12 hours of storage. Then slides were prepared after 3 and 6 weeks. In addition slides were prepared from UCM 141 and 149 after 6 weeks at RT. The slides were prepared by spotting 200 µl of cell suspension onto polycarbonate filter. The filter was then placed on the glass slide and blotted. The filter was then removed and the slides fixed in 95% ethanol for 5 minutes. The slides were stained using routine Papanicolaou staining and Hematoxylin and Eosin (H&E). The slides were evaluated under a light microscope using different magnifications, and documentation in the form of color pictures was prepared. Additionally a smaller study was performed using a mixture of normal human cervical cells and CaSki cells. This mixture was placed in two UCM formulations 141 and 149 and in PreservCyt and CytoRich controls. Each sample was split into two tubes and placed at RT and at 4° C. After 12 hours (baseline), 10 days and three weeks of storage, slides were prepared and stained with Papanicolaou staining. The following features were evaluated for the morphology study: cell dispersion, cell shape, nuclear shape, chromatin pattern and staining intensity, nuclear/cytoplasm ratio, presence of nucleoli, cytoplasm shape and staining color. FIGS. 1-17 show the morphology of CaSki cells stored in different UCM and in PreservCyt and CytoRich controls stored at RT for 12 hours, 3 weeks and 6 weeks. All features characteristic for CaSki cells (carcinoma cells) were visible and well preserved in all fixatives tested after 3 and 6 weeks: large and hyperchromatic nuclei usually with oval shape and irregular granular chromatin, scanty cytoplasm, multinucleated cells, presence of nucleoli and presence of mitotic figures. In addition, the slides showed that there was good cell dispersion and no cell clumping in all media tested.

FIGS. 18-41 show the morphology of normal human cervical cells mixed with CaSki cells and stored in UCM 141, 149 and PreservCyt and CytoRich controls for 12 hours, 10 days and 3 weeks at room temperature and at 4° C. The evaluation of these slides showed that the morphology was well preserved in UCM and in PreservCyt and CytoRich controls. After 3 weeks at 4° C. and room temperature both types of cells (normal cervical and CaSki cells) had distinct and sharp shapes (both nuclei and cytoplasm). The nuclei were well stained and the normal cells showed a different color of cytoplasm depending on the maturity.

Figure 42:
FIG. 42. Conventional Pap smear (archival). Magnification×120.

FIG. 42 was taken from an archived routine Pap smear to show the morphology and staining of samples stored fixed to slides for comparison.

Example 3

HC II HPV DNA Assay Results

UCM formulations 127, 128, 130 and the STM™ (Digene) control were tested using the Hybrid Capture II HPV DNA Test. A standard HC II HPV Test kit (Digene catalog number 5101-1096) was used. Each collection medium (1 mL) was spiked with $0.8 \times 10^6$ CaSki cells (~500 copies/cell). This concentration of CaSki cells was chosen because an adequate clinical specimen usually contains about $1 \times 10^6$ cells. The same stock of CaSki cells was then used for morphology study and DNA and RNA testing. A standard volume of 50 μl was used per assay as described in the Package Insert, without any sample preparation modification. A similar STM sample was prepared by spiking the same number of CaSki cells into 1 mL of Digene Sample Transport Medium (STM—this medium is the current medium used for HPV testing. It preserves DNA and RNA but not cell morphology). The HC II HPV test was performed at day "0" (baseline) and after one and six weeks of storage at room temperature. Table 1 shows the results obtained for each medium at the baseline and after one and six weeks expressed as S/N ratios.

UCM formulations 127 and 128 had the highest S/N ratios comparable to the STM control S/N ratios at the baseline and retained these values after storage at RT for six weeks. The S/N ratios for UM 130 obtained at the baseline were slightly lower when compared to UCM 127 and 128. UCM 130 retained its signal after 6 weeks.

TABLE 1

Signal to Noise ratios obtained for UCM 127, 128, 130 and STM at baseline and after one week and six weeks storage at RT.

| Medium | Baseline S/N | Week 1 S/N | Week 1 % of original signal | Week 6 S/N | Week 6 % of original signal |
|---|---|---|---|---|---|
| 127 | 5666 | 5852 | 103 | 6298 | 111 |
| 128 | 5760 | 5669 | 98 | 5932 | 103 |
| 130 | 4407 | 5135 | 117 | 5500 | 125 |
| STM | 5557 | 6151 | 110 | 6127 | 110 |

Formulations UCM 141 and 149, used in the smaller morphology study, were tested in the HC II HPV DNA assay at baseline and then after one, two and four weeks of storage at room temperature. CaSki cells ($1.5 \times 10^6$) were spiked in these media and 50 μl were used per assay. Table 2 shows the S/N ratios. Both formulations retained close to 100% (UCM 141 98.4% and UCM 149 97.3%) of the original signal after four weeks of storage at room temperature.

TABLE 2

S/N ratios obtained for formulations UC 141 and 149 at baseline and after 1, 2 and 4 weeks of storage at RT.

| UCM | Baseline S/N | Week 1 S/N | Week 1 % original signal | Week 2 S/N | Week 2 % original signal | Week 4 S/N | Week 4 % original signal |
|---|---|---|---|---|---|---|---|
| 141 | 10875 | 11006 | 101.2 | 10427 | 95.9 | 10703 | 98.4 |
| 149 | 9443 | 8159 | 86.4 | 8035 | 85.3 | 9188 | 97.3 |

In addition, samples stored in PreservCyt and CytoRich were examined according to the protocols of this example. Both the PreservCyt and CytoRich media were found to be deficient in their ability to provide DNA for satisfactory analysis.

Example 4

HC II RNA Assay Results

The aliquots of all formulations (CaSki cells $0.8 \times 10^6$) were stored at 4° C. instead of room temperature and were tested in the HC II HPV RNA assay. The prototype RNA assay used in this study utilized biotinylated single-stranded DNA probes specific for HPV 16 E6/E7 RNA. UCM formulations 127, 128 and 130 were tested at baseline and after one and six weeks storage at 4° C. UCM formulations 141 and 149 were tested at baseline and after one, two and four weeks of storage at 4° C. Tables 3 and 4 show the results.

TABLE 3

Results obtained for UCM 127, 128 and 130 in HC II RNA assay at baseline and after one and six weeks of storage at 4° C.

| Medium | Baseline S/N | Week 1 | | Week 6 | |
|---|---|---|---|---|---|
| | | S/N | % original signal | S/N | % original signal |
| 127 | 937 | 1157 | 123 | 990 | 106 |
| 128 | 981 | 1139 | 116 | 1192 | 122 |
| 130 | 845 | 1261 | 149 | 1278 | 151 |

All UCM formulations tested had comparable S/N ratios when tested at the baseline. UCM 127, 128 and 130 retained a 100% signal after six weeks of storage at 4° C. in comparison to baseline results. RNA in cells in both UCM formulations 141 and 149 appears to be stable at 4° C. for four weeks giving S/N ratios close to the baseline results (UCM 141 108% and UCM 149 89%).

TABLE 4

Results obtained for UCM 141 and 149 in HC II RNA assay at baseline and after one, two and four weeks of storage at 4° C.

| UCM | Baseline S/N | Week 1 | | Week 2 | | Week 4 | |
|---|---|---|---|---|---|---|---|
| | | S/N | % original signal | S/N | % original signal | S/N | % original signal |
| 141 | 1074.5 | 1029 | 96 | 1137 | 106 | 1164 | 108 |
| 149 | 1243.5 | 1786 | 144 | 1843 | 148 | 1103 | 89 |

In addition, samples stored in PreservCyt and CytoRich were examined according to the protocols of this example. Both the PreservCyt and CytoRich media were found to be deficient in their ability to provide RNA for satisfactory analysis.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

Birkenmeyer & Mushahwar, *J. Virol. Meth.*, 35:117-126 (1991)
Chernoff et al. *J. Clinical Microbiology* 35(11):2740-2744 (1997)
Cope et al. *J. Clin. Microbiol.* 35(9):2262-2265 (1997)
Cullen et al., *J. Virol.* 65(2):606-612 (1991)
Demeret et al., *J. Virol.* 68(1):7075-7082 (1994)
Dürst et al., *J. Gen. Virol.* 66:1515-1522(1985)
Jeon et al., *J. Virol.* 69(5):2989-2997 (1995)
Landegren, *Trends Genetics*, 9(6):199-204 (1993)
Leiserowitz et al. *Gynecol. Oncol.* 66(2):295-299 (1997)
Lizard et al. *Histochem J.* 29(7):545-554 (1997)
Mant et al. *J. Virol. Meth.* 66(2):169-178 (1997)
Matsukura et al., *Virology* 172(1):63-72 (1989)
Nuovo, PCR In Situ Hybridization: Protocols and Applications, 3rd Edition, Lippencott-Raven Publishers, Philadelphia 1997
Schneider-Gädicke et al. *EMBO J.* 5:2285-2292 (1986)
Schwarz, et al., *Nature* 314:111-114 (1985)
Stoflet et al. *Science* 239:491-494 (1988)
Swan et al. *J. Clin. Microbiol.* 35(4):886-891 (1997)
Turek, *Adv Virus Res.* 44:305-356 (1994)
Ushikai et al., *J. Virol.* 68(1):6655-6666 (1994)
Wilczynski et al., *Virology* 166:624-267 (1988)
Zehbe (1) et al. *Am. J. Pathol.* 150(5): 1553-1561 (1997)
Zehbe (2) et al. *Mod. Pathol.* 10(3):188-91(1997)

We claim:

1. A cell collection medium, wherein the cells contained in the medium can be analyzed directly by both cytological and molecular methods, wherein the molecular method of analysis comprises either RNA or DNA or protein analysis or the analysis of both RNA and DNA, wherein the medium is water based and comprises a buffer component, at least one alcohol, a non-crosslinking fixative and an agent to inhibit degradation of at least one of RNA, DNA, or protein, wherein the non-crosslinking fixative comprises about 1% to about 15% of the medium, and wherein the buffer component has a buffering capacity within a pH range of about 3 to about 5.

2. The medium of claim 1, wherein the buffer component has a buffering capacity within a pH range of about 3.5 to about 4.5.

3. The medium of claim 1, wherein the alcohol component comprises a C1 to C10 alcohol.

4. The medium of claim 3, wherein the alcohol component is selected from the group consisting of methanol, ethanol, propanols, butanols, and pentanols.

5. The medium of claim 4, wherein the alcohol component comprises ethanol or n-butanol.

6. The medium of claim 1, wherein the fixative comprises a polymer selected from the group consisting of a poly(ethylene glycol) and a poly(ethylene oxide).

7. The medium of claim 1, wherein the fixative is a poly(ethylene glycol).

8. The medium of claim 7, wherein the poly(ethylene glycol) has a molecular weight of between about 600 and about 4600.

9. The medium of claim 8, wherein the poly(ethylene glycol) has a molecular weight of about 1500.

10. The medium of claim 1, wherein the agent to inhibit degradation of at least one of the group consisting of RNA, DNA, and protein comprises at least one agent selected from the group consisting of a nuclease inhibitor, a protease inhibitor and a chelating agent.

11. The medium of claim 10, wherein the agent to inhibit degradation of at least one of the group consisting of RNA, DNA, and protein comprises a chelating agent.

12. The medium of claim 11, wherein the chelating agent is selected from the group consisting of murexide, chromotropic acid, 1-(1-hydroxy-2-napththylazo-2-hydroxy-5-nitronaphthalene-4-sulphonic acid, ethylenediaminetetraacetic acid, o-phenanthroline, and thiourea.

13. The medium of claim 12, wherein the chelating agent comprises ethylenediaminetetraacetic acid.

14. The medium of claim 1, wherein the alcohol is selected from the group consisting of methanol, ethanol, propanols, butanols, and pentanols, wherein the agent to inhibit degradation is a chelating agent selected from the group consisting of murexide, chromotropic acid, 1-(1-hydroxy-2-napththylazo-2-hydroxy-5-nitronaphthalene-4-sulphonic acid, ethylenediaminetetraacetic acid, o-phenanthroline, and thiourea, and wherein the fixative comprises a polymer selected from the group consisting of a poly(ethylene glycol) and a poly(ethylene oxide).

* * * * *